United States Patent
Yoon et al.

(10) Patent No.: US 10,565,748 B2
(45) Date of Patent: Feb. 18, 2020

(54) MEDICAL IMAGING APPARATUS AND METHOD OF OPERATING THE SAME

(71) Applicant: Samsung Electronics Co., Ltd., Suwon-si, Gyeonggi-do (KR)

(72) Inventors: Hui-su Yoon, Gwacheon-si (KR); Sang-nam Nam, Suwon-si (KR); Kyoung-yong Lee, Hwaseong-si (KR); Dong-gue Lee, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 124 days.

(21) Appl. No.: 15/829,649

(22) Filed: Dec. 1, 2017

(65) Prior Publication Data

US 2018/0158218 A1 Jun. 7, 2018

(30) Foreign Application Priority Data

Dec. 2, 2016 (KR) .................. 10-2016-0163893

(51) Int. Cl.
| | | |
|---|---|---|
| *G06K 9/00* | (2006.01) | |
| *G06T 11/00* | (2006.01) | |
| *G06T 5/00* | (2006.01) | |
| *A61B 6/00* | (2006.01) | |
| *G06T 5/20* | (2006.01) | |
| *A61B 6/03* | (2006.01) | |
| *G06T 3/40* | (2006.01) | |

(52) U.S. Cl.
CPC ............ *G06T 11/008* (2013.01); *A61B 6/032* (2013.01); *A61B 6/501* (2013.01); *A61B 6/5205* (2013.01); *A61B 6/5258* (2013.01); *G06T 3/4007* (2013.01); *G06T 5/002* (2013.01); *G06T 5/20* (2013.01); *G06T 11/005* (2013.01); *G06T 11/006* (2013.01); *G06T 2207/10081* (2013.01)

(58) Field of Classification Search
CPC ....... G06T 11/008; G06T 3/4007; G06T 5/20; G06T 11/005; G06T 5/002; G06T 11/006; G06T 2207/10081; A61B 6/5258; A61B 6/5205; A61B 6/501; A61B 6/032
USPC ...................................................... 382/131
See application file for complete search history.

(56) References Cited

U.S. PATENT DOCUMENTS 6,721,387 B1 * 4/2004 Naidu .................. A61B 6/032
378/4
7,340,027 B2 3/2008 Timmer
(Continued)

FOREIGN PATENT DOCUMENTS

| KR | 10-2010-0045277 A | 5/2010 |
|---|---|---|
| KR | 10-2011-0040164 A | 4/2011 |

OTHER PUBLICATIONS

May Oehler et al, "Evaluation of Surrogate Data Quality in Sinogram-Based CT Metal-Artifact Reduction, 2008", Proc. of SPIE, vol. 7076, pp. 707607-1-707607-10 (Year: 2008).*

(Continued)

*Primary Examiner* — Van D Huynh

(57) ABSTRACT

Provided is a computed tomography (CT) imaging apparatus, the CT imaging apparatus including a data obtainer configured to obtain first raw data from X-ray transmitted by an object; and a processor configured to interpolate a pixel value corresponding to a to-be-restored region within raw data, based on a pixel value of at least one line that penetrates through the to-be-restored region.

20 Claims, 15 Drawing Sheets

(56) References Cited

U.S. PATENT DOCUMENTS

| | | | |
|---|---|---|---|
| 8,233,586 B1 | 7/2012 | Boas | |
| 8,280,135 B2 | 10/2012 | McCollough et al. | |
| 2003/0219093 A1* | 11/2003 | Hagiwara | G06T 11/005 378/4 |
| 2009/0074278 A1* | 3/2009 | Beaulieu | A61B 6/032 382/131 |
| 2011/0007956 A1* | 1/2011 | Meyer | A61B 6/032 382/131 |
| 2011/0081071 A1* | 4/2011 | Benson | G06T 11/005 382/154 |
| 2015/0146955 A1* | 5/2015 | Dong | G06T 11/008 382/131 |
| 2017/0273654 A1* | 9/2017 | Taguchi | A61B 6/5258 |

OTHER PUBLICATIONS

May Oehler et al., "Evaluation of Surrogate Data Quality in Sinogram-Based CT Metal-Artifact Reduction", Proc. of SPIE, vol. 7076, 2008, 10 pages.

Oliver Watzke et al., "A pragmatic approach to metal artifact reduction in CT: merging of metal artifact reduced images", European Radio, Jan. 1, 2004, 8 pages.

Philippe P. Bruyant et al., "Streak Artifact Reduction in Filtered Backprojection Using a Level Line-Based Interpolation Method", Streak Artifact Reduction, Nov. 2000, p. 1913-1919.

European Search Report dated May 2, 2018 in connection with European Patent Application No. 17 20 4864.

Communication pursuant to Article 94(3) EPC dated Mar. 20, 2019 in connection with European Patent Application No. 17 204 864.7, 5 pages.

* cited by examiner

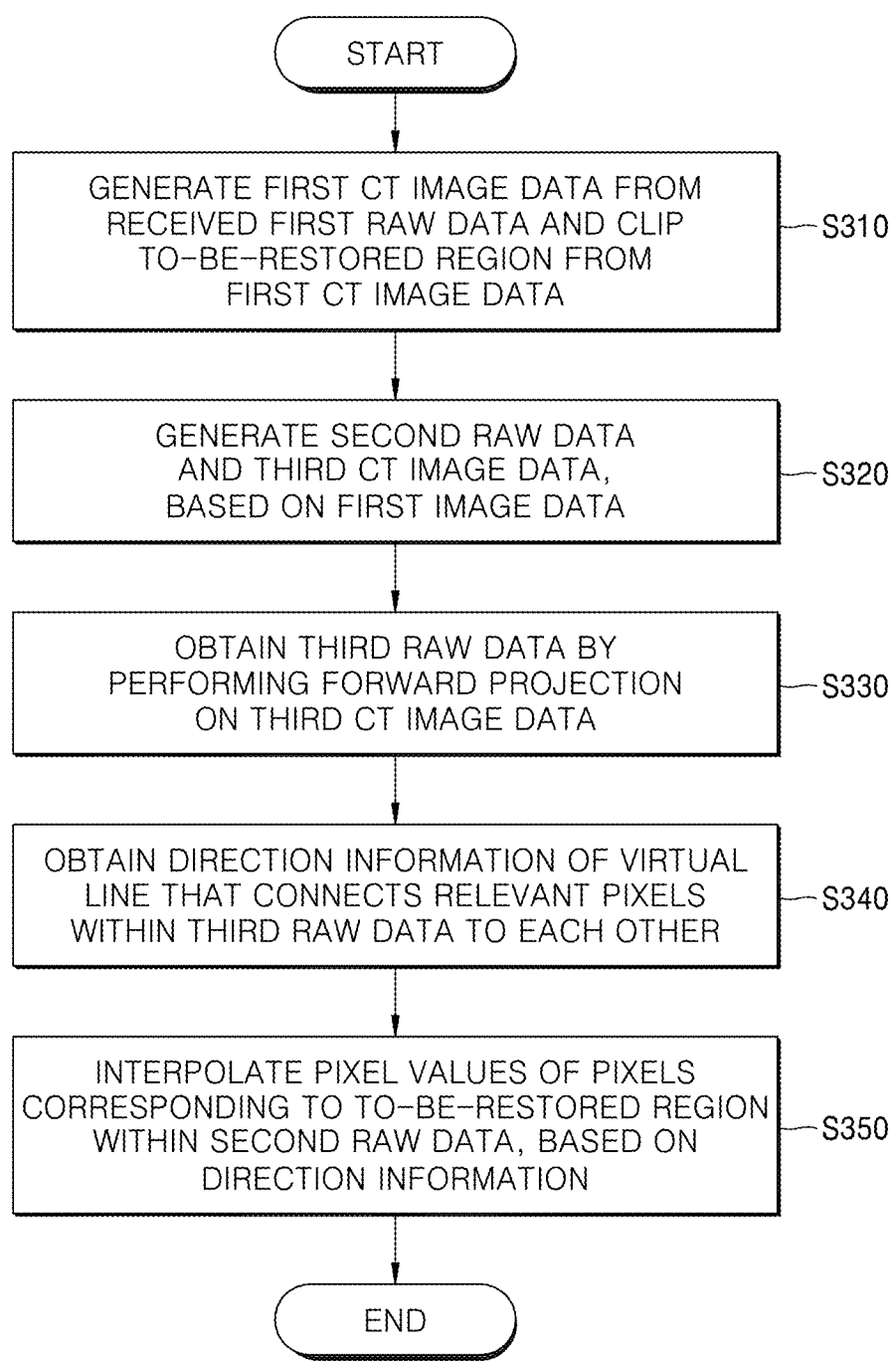

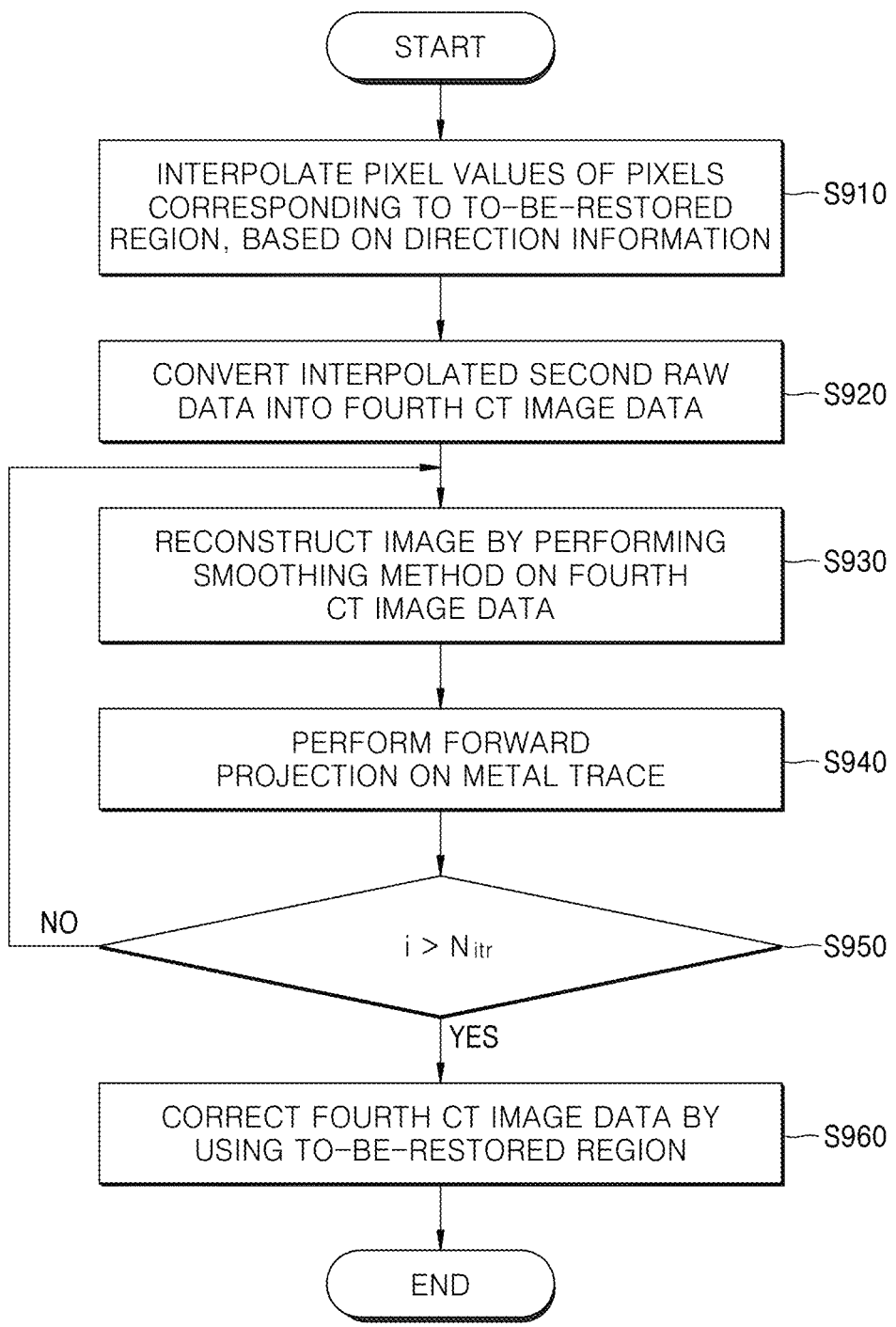

MEDICAL IMAGING APPARATUS AND METHOD OF OPERATING THE SAME

CROSS-REFERENCE TO RELATED APPLICATION AND CLAIM OF PRIORITY

This application is related to and claims priority to Korean Patent Application No. 10-2016-0163893, filed on Dec. 2, 2016, the contents of which are incorporated herein by reference.

TECHNICAL FIELD

The present disclosure relates to a medical imaging apparatus and a method of operating the same, and more particularly, to an apparatus and method of reducing metal artifacts generated during processing of a computed tomography (CT) image.

BACKGROUND

Medical imaging apparatuses are equipment for capturing images of an internal structure of an object. Medical imaging apparatuses are noninvasive examination apparatuses that capture and process images of the structural details of a human body, internal tissue thereof, and fluid flow within a human body and provide the processed images to a user. A user, such as a doctor, may diagnose a health state and a disease of a patient by using a medical image output from a medical imaging apparatus.

Representative examples of apparatuses for radiating X-rays onto a patient to scan an object include computed tomography (CT) apparatuses. CT apparatuses are capable of providing a cross-sectional image of an object and distinctively expressing inner structures (e.g., organs such as a kidney, a lung, etc.) of the object, compared to general X-ray apparatuses. Thus, CT apparatuses are widely used for accurately diagnosing a disease.

CT apparatuses may detect X-rays transmitted through an object by using an X-ray detector and may perform image processing on raw data obtained using the detected X-rays, thereby reconstructing an accurate CT image. When the object from which the CT image is captured includes an object having a significantly higher density than a neighboring body tissue, for example, a metallic implant, beam hardening, beam scatter, streak artifacts may occur in the CT image due to a relatively very large attenuation coefficient. Accordingly, when the CT image is reconstructed, metal artifacts may occur in a region where the metallic implant is and in a direction that the metal implant passes through. The metal artifacts may make the CT image unclear and may reduce readability

SUMMARY

To address the above-discussed deficiencies, it is a primary object to provide metal artifact reduction (MAR) methods and apparatuses for reducing metal artifacts in reconstructing a computed tomography (CT) image from raw data obtained from X-rays transmitted through an object.

Additional aspects will be set forth in part in the description which follows and, in part, will be apparent from the description, or may be learned by practice of the presented embodiments.

According to an aspect of an embodiment, a method of operating a CT imaging apparatus includes generating first CT image data from first raw data received from an X-ray detector and clipping a to-be-restored region from the first CT image data; generating second raw data and third CT image data, based on the first CT image data from which the to-be-restored region was clipped; obtaining third raw data by performing forward projection on the third CT image; obtaining direction information of a virtual line that connects pixels that are relevant based on pixel values of a plurality of pixels included in the third raw data; and interpolating a pixel value of a pixel corresponding to the to-be-restored region within the second raw data, based on the direction information.

According to an aspect of an embodiment, a computed tomography (CT) imaging apparatus includes a data obtainer configured to obtain first raw data from an X-ray transmitted by an object; and a processor configured to generate first CT image data from the first raw data, set and clip a to-be-restored region from the first CT image data, generate second raw data and third CT image data based on the first CT image data from which the to-be-restored region was clipped, obtain third raw data by performing forward projection on the third CT image data, obtain direction information of a virtual line that connects relevant pixels based on pixel values of a plurality of pixels included in the third raw data, and interpolate a pixel value of a pixel corresponding to the to-be-restored region within the second raw data, based on the direction information.

According to an aspect of an embodiment, a computer-readable recording medium has recorded thereon a program for executing a method of operating the CT imaging apparatus.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 3 is a flowchart illustrating a method in which the CT imaging apparatus interpolates metal artifacts from raw data, according to an embodiment of the present disclosure;

FIG. 9 is a flowchart illustrating a method in which the CT imaging apparatus generates a final CT image by reconstructing interpolated raw data image, according to an embodiment of the present disclosure.

DETAILED DESCRIPTION

Figure 1:
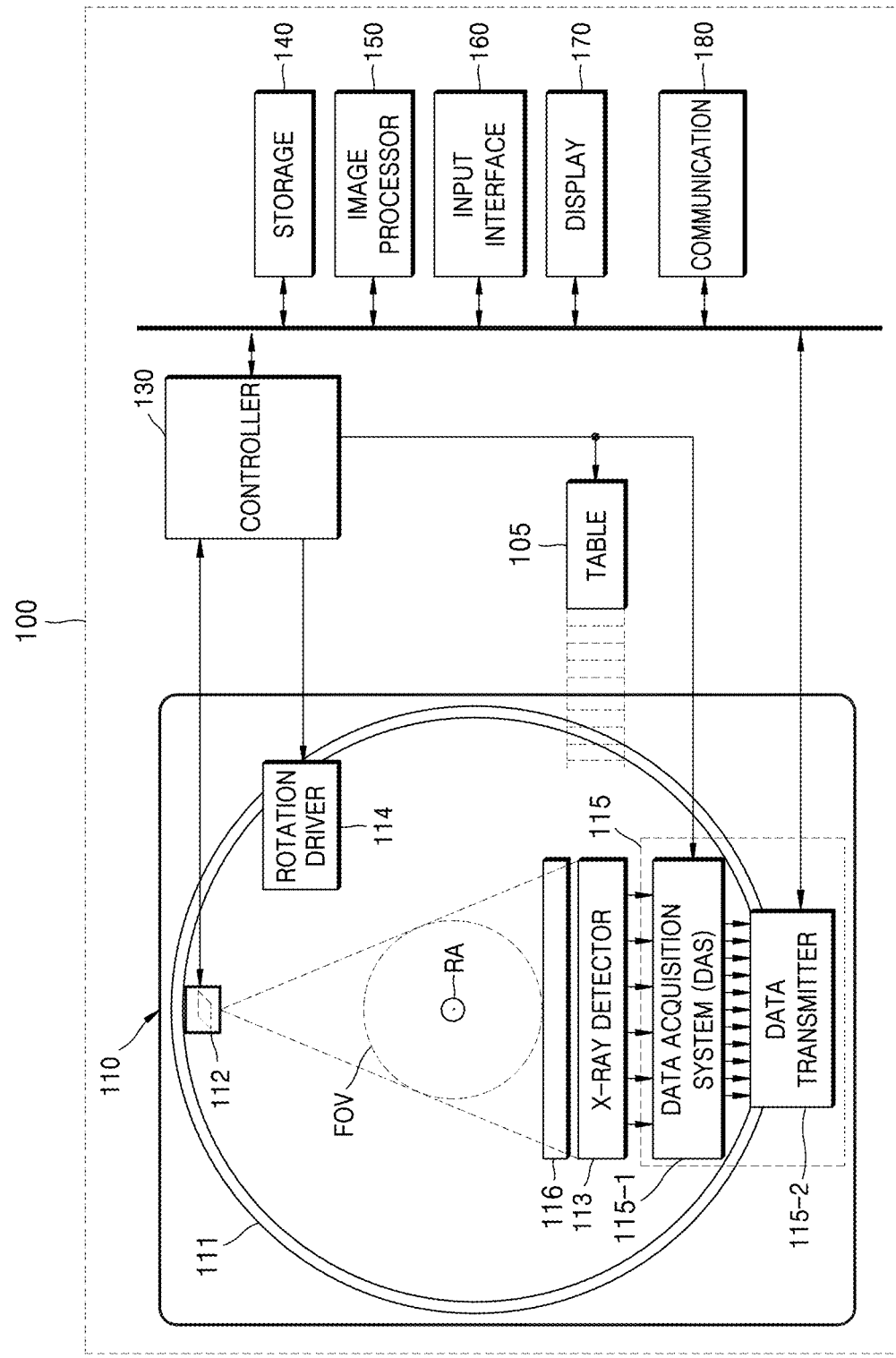
FIG. 1 is a block diagram illustrating a structure of a computed tomography (CT) imaging apparatus according to an embodiment of the present disclosure.

FIGS. 1 through 9, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Throughout the specification, like reference numerals or characters refer to like elements. In the present specification, all elements of embodiments are not explained, but general matters in the technical field of the present disclosure or redundant matters between embodiments will not be described. Terms 'part' and 'portion' used herein may be implemented using software or hardware, and, according to embodiments, a plurality of 'parts' or 'portions' may be implemented using a single unit or element, or a single 'part' or 'portion' may be implemented using a plurality of units or elements. The operational principle of the present disclosure and embodiments thereof will now be described more fully with reference to the accompanying drawings.

In the present specification, an image may include a medical image obtained by a medical imaging apparatus, such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

FIG. 1 illustrates a structure of a CT system 100 according to an embodiment.

The CT system 100 may include a gantry 110, a table 105, a controller 130, a storage 140, an image processor 150, an input interface 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays.

The CT system 100 may be implemented as a single-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program codes for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomography image, to thereby generate the tomography data. According to an embodiment, the tomography data may be in the form of data that has undergone back-projection, or in the form of a tomography image. According to embodiments, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, etc., and may include a volatile or non-volatile storage medium.

The input interface 160 receives control signals, data, etc., from a user. The display 170 may display information indicating an operational status of the CT system 100, medical information, medical image data, etc.

The CT system 100 includes the communication interface 180 and may be connected to external devices, such as a server, a medical apparatus, and a portable device (smartphone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

The communication interface 180 may receive control signals and data from an external device and transmit the received control signals to the controller 130 so that the controller 130 may control the CT system 100 according to the received control signals.

Alternatively, by transmitting a control signal to an external device via the communication interface 180, the controller 130 may control the external device according to the control signal.

For example, the external device may process data according to a control signal received from the controller 130 via the communication interface 180.

A program for controlling the CT system 100 may be installed on the external device and may include instructions for performing some or all of the operations of the controller 130.

The program may be preinstalled on the external device, or a user of the external device may download the program from a server that provides an application for installation. The server that provides an application may include a recording medium having the program recorded thereon.

According to embodiments, the CT system 100 may or may not use contrast media during a CT scan, and may be implemented as a device connected to other equipment.

Figure 2:
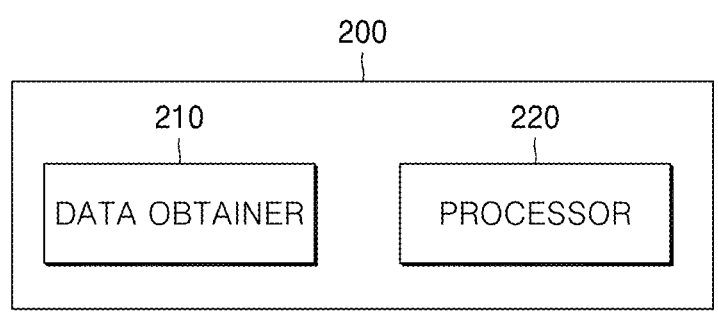
FIG. 2 is a block diagram illustrating a CT imaging apparatus according to an embodiment of the present disclosure.

FIG. 2 is a block diagram illustrating a computed tomography (CT) imaging apparatus 200 according to an embodiment of the present disclosure.

Referring to FIG. 2, the CT imaging apparatus 200 may include a data obtainer 210 and an image processor 220. Although FIG. 2 illustrates components used to explain the CT imaging apparatus 200 according to an embodiment of the present disclosure, the CT imaging apparatus 200 may further include components included in the CT system 100 of FIG. 1.

The data obtainer 210 may receive X-rays radiated onto an object from the X-ray detector 113 of FIG. 1 and may amplify an X-ray signal to thereby obtain raw data about the object. According to an embodiment, the data obtainer 210 may receive X-ray raw data from an external source via the communication interface 180 of FIG. 1.

The processor 220 reconstructs the raw data obtained by the data obtainer 210 by using a method, such as processing and image processing, to thereby generate CT image data. The processor 220 may include a hardware component, such as a field-programmable gate array (FPGA) or an application-specific integrated circuit (ASIC). The processor 220 may include at least one of a central processing unit (CPU), a microprocessor, and a graphics processing unit (GPU). The processor 220 may be a hardware unit including a processor and a memory. However, the processor 220 is not limited thereto, and the processor 220 may be any other hardware device capable of processing and image-processing the raw data.

According to an embodiment, the raw data received by the processor 220 may be a sinogram. The processor 220 may reconstruct received first raw data to generate first CT image data. According to an embodiment, the processor 220 may generate the first raw data according to a method using a filtered back-projection (FBP) algorithm.

The processor 220 may set a to-be-restored region from the first CT image data and clip the to-be-restored region from the first CT image data. According to an embodiment, the processor 220 may clip, from the first CT image data, only a region of which a data value representing an attenuation degree of X-ray transmitted by the object exceeds a preset threshold. The processor 220 may use a Hounsfield unit (HU) to clip the to-be-restored region. The HU expresses, as a relative figure, the degree to which X-ray is attenuated according to an absorption degree based on a density difference of a specific material when an X-ray is transmitted by the specific material. As the value of the HU increases, X-ray attenuation, namely, a degree to which an X-ray is blocked, increases. For example, water may have a value of 0 HU, air may have a value of −1000 HU, a soft tissue of a human being may have a value between 10 HU and 30 HU, and a bone of a human being may have a value of 1000 HU. The to-be-restored region may include a metal artifact, due to for example, a metallic implant having a value of about 3000 HU or greater. A method in which the processor 220 clips a to-be-restored region will be described later in detail with reference to FIG. 4A.

The processor 220 may generate second raw data by performing forward projection on the first CT image data from which the to-be-restored region was clipped, and may interpolate pixel values of pixels corresponding to a to-be-restored region included in the second raw data. According to an embodiment, the processor 220 may interpolate the pixels corresponding to the to-be-restored region included in the second raw data, by performing linear interpolation.

The processor 220 may generate second CT image data by performing FBP on the second raw data reconstructed via the interpolation. The processor 220 may generate a split image from the second CT image data according to the data value representing the attenuation degree of the X-ray transmitted through the object. According to an embodiment, the processor 220 may set a minimum or maximum value of the attenuation degree of the X-ray transmitted by the object, namely, the HU, and may split only a tissue region corresponding to a value greater than the preset minimum value or smaller than the preset maximum value from the object. According to an embodiment, the split image may include a soft tissue or a bone.

The processor 220 may obtain third raw data by performing forward projection on the split image. The processor 220 may obtain direction information of a virtual line that connects pixels that are relevant based on the pixel values of a plurality of pixels included in the obtained third raw data. In detail, the processor 220 may obtain direction information of a virtual line that connects a first pixel from among the plurality of pixels included in the third raw data to a second pixel whose pixel value varies the least relative to a pixel value of the first pixel from among pixels that are adjacent to the first pixel in a first direction and a second direction. According to another embodiment, the processor 220 may obtain direction information of a virtual line that connects a first pixel from among the plurality of pixels included in the third raw data to a second pixel whose pixel value is similar to the pixel value of the first pixel from among the pixels that are adjacent to the first pixel in the first direction and the second direction. A method in which the processor 220 obtains the direction information from the third raw data will be described later in detail with reference to FIG. 6B.

The processor 220 may interpolate the pixel values of the pixels corresponding to the to-be-restored region within the second raw data, based on the direction information obtained from the third raw data. According to an embodiment, the processor 220 may interpolate the pixel values of the pixels corresponding to the to-be-restored region, by performing at least one of linear interpolation, spline interpolation, and polynomial interpolation.

In restoring a CT image from raw data, in the case of important surgery performed in units of millimeters (mm), the size of a metal artifact generated due to a metallic implant needs to be accurately measured. In addition, when a CT image is restored, banding artifacts generated in a bright or dark area around metal artifacts may impede accurate surgery. The CT imaging apparatus 200 according to an embodiment of the present disclosure may interpolate a pixel of a to-be-restored region that needs to be restored due to metal artifacts, based on prior data of raw data (for example, a sinogram), namely, direction information obtained before restoring the CT image, thereby improving the accuracy of restoring a CT image and the performance of MAR.

FIG. 3 is a flowchart illustrating a method in which the CT imaging apparatus 200 of FIG. 2 interpolates metal artifacts from raw data, according to an embodiment of the present disclosure.

In operation S310, the CT imaging apparatus 200 generates the first CT image data from the received first raw data and clips the to-be-restored region from the first CT image data. According to an embodiment, the received first raw data may be a sinogram that is obtained from X-ray transmitted by the object and detected by the X-ray detector 113 of FIG. 1 and is output by the data acquisition system 115-1 of FIG. 1. According to an embodiment, the CT imaging apparatus 200 may generate the first CT image data by applying FBP to the first raw data. The CT imaging apparatus 200 sets the to-be-restored region from the first CT image data and clips the set to-be-restored region from the first CT image data. The CT imaging apparatus 200 may set a region having an HU that is equal to or greater than a preset threshold, as the to-be-restored region from the first CT image data. For example, the to-be-restored region may be a metal artifact, such as a metallic implant having a value of about 3000 HU or greater.

According to an embodiment, the CT imaging apparatus 200 may clip the set to-be-restored region from the first CT image data.

In operation S320, the CT imaging apparatus 200 generates the second raw data and the third CT image data, based on the first CT image data. According to an embodiment, the CT imaging apparatus 200 may generate the second raw data by performing forward projection on the first CT image data from which the to-be-restored region was clipped.

In operation S330, the CT imaging apparatus 200 obtains the third raw data by performing forward projection on the third CT image data.

In operation S340, the CT imaging apparatus 200 obtains the direction information of a virtual line that connects relevant pixels within the third raw data to each other. According to an embodiment, the CT imaging apparatus 200 may obtain direction information of a virtual line that connects pixels having pixel values between which a variation is smallest from among the plurality of pixels included in the third raw data. The CT imaging apparatus 200 may obtain direction information of a virtual line that connects pixels having similar pixel values from among the plurality of pixels included in the third raw data.

In operation S350, the CT imaging apparatus 200 interpolates the pixel values of the pixels corresponding to the to-be-restored region within the second raw data, based on the direction information. According to an embodiment, the CT imaging apparatus 200 may interpolate the pixel values of the pixels corresponding to the to-be-restored region by performing linear interpolation within the second raw data by using pixel values of adjacent neighboring pixels based on the direction information obtained in operation S340.

The CT imaging apparatus 200 may use one interpolation method from among a linear interpolation method in which a function passing between pixels is obtained and interpolated using a linear equation, polynomial interpolation in which a pixel value is interpolated by expressing a polynomial equation passing (n+1) pixels in a polynomial equation of an n-th degree or smaller, and spline interpolation in which a polynomial equation is applied to a subset of pixel values. Linear interpolation, polynomial interpolation, and spline interpolation are well known to one of ordinary skill in the art to which the present disclosure pertains, and thus detailed descriptions thereof will be omitted.

However, embodiments are not limited thereto, and the CT imaging apparatus 200 may interpolate a pixel value by using any other well-known interpolation method.

Figure 4A:
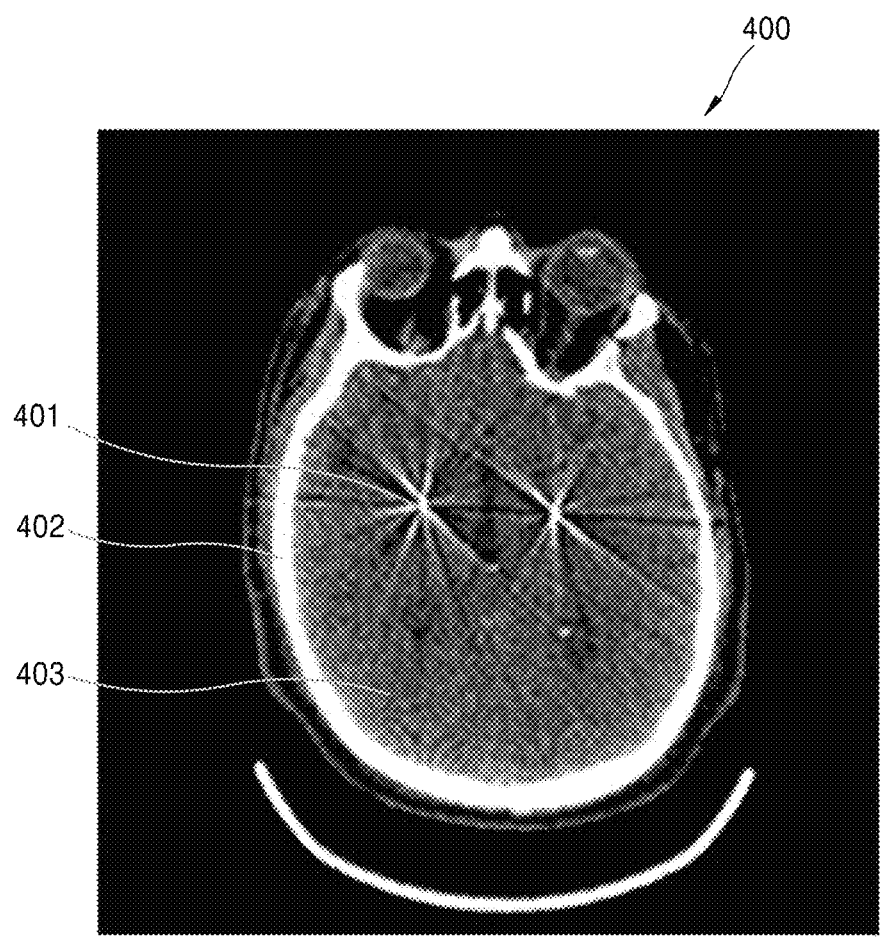
FIGS. 4A-4C are views illustrating a method in which the CT imaging apparatus clips a to-be-restored region generated due to metal artifacts and interpolates pixels corresponding to the to-be-restored region, according to an embodiment of the present disclosure.

FIG. 4A is an image illustrating a method in which the CT imaging apparatus 200 of FIG. 2 clips a to-be-restored region generated due to metal artifacts, according to an embodiment of the present disclosure.

FIG. 4A illustrates a first CT image 400 obtained by the CT imaging apparatus 200 performing FBP on first raw data received from X-ray transmitted by the head of a person. Referring to FIG. 4A, the first CT image 400 may include images of a metallic implant 401, a bone 402, and a soft tissue 403. X-ray has different attenuation degrees according to absorption degrees based on a difference between densities of tissues within an object. Accordingly, the metallic implant 401, the bone 402, and the soft tissue 403 within the first CT image 400 may be displayed in different brightness levels.

In general, because the metallic implant 401 has a value of about 3000HU or greater, the metallic implant 401 may be displayed most brightly. In FIG. 4A, the metallic implant 401 is displayed as two points. There is a relatively bright or dark region that spreads from the two points representing the metallic implant 401 in all directions. This region is a metal artifact generated due to the metallic implant 401, and may make it difficult for a user (for example, a doctor) to read the first CT image 400.

Figure 4B:
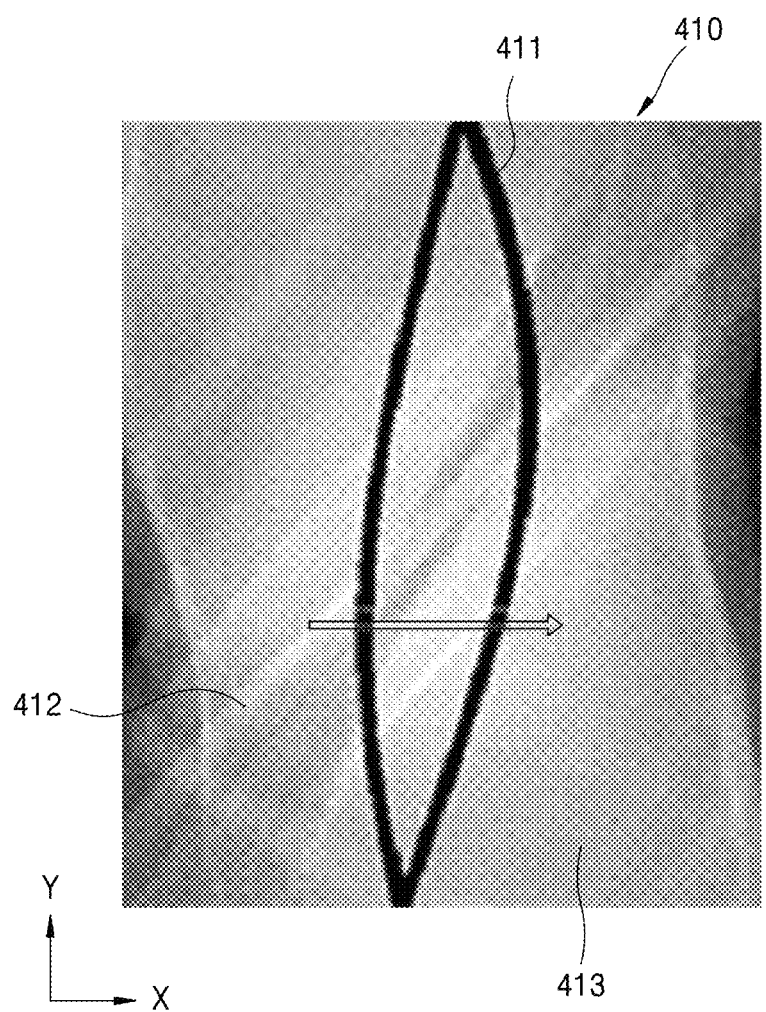

FIG. 4B illustrates a sinogram 410 that the CT imaging apparatus 200 generates by clipping the to-be-restored region from the first CT image 400 of FIG. 4A and then reconstructing the first CT image 400. Referring to FIG. 4B, the sinogram 410 may include a metal trace 411, first pixel data 412 corresponding to the bone 402 of FIG. 4A, and second pixel data 413 corresponding to the soft tissue 403 of FIG. 4A.

The CT imaging apparatus 200 may set the metallic implant 401 in the first CT image 400 as a to-be-restored region and split the to-be-restored region from the first CT image 400. In FIG. 4B, the to-be-restored region may be the metal trace 411 generated due to the metallic implant 401 of FIG. 4A.

The CT imaging apparatus 200 may process pixel values of pixels corresponding to the metal trace 411 in the sinogram 410 to 'null' or '0', and may interpolate the pixels corresponding to the metal trace 411, based on pixel values of pixels that are adjacent to the pixels corresponding to the metal trace 411 in the first direction (X direction). According to an embodiment, the CT imaging apparatus 200 may interpolate the pixel values corresponding to the metal trace 411 by performing linear Interpolation.

Figure 4C:
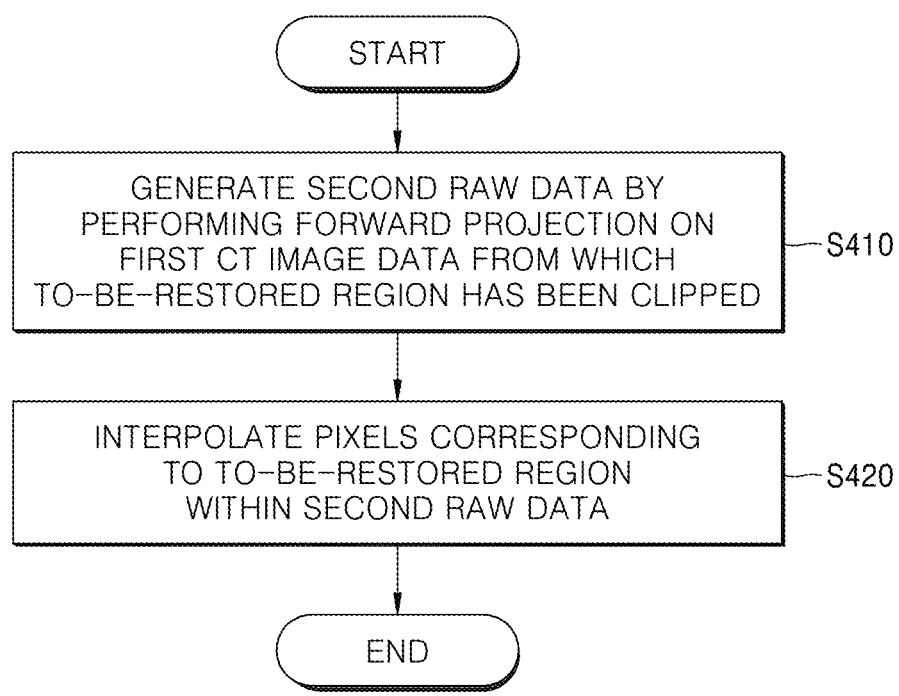

FIG. 4C is a flowchart illustrating a method in which the CT imaging apparatus 200 of FIG. 2 clips a to-be-restored region generated due to metal artifacts and interpolates pixels corresponding to the to-be-restored region, according to an embodiment of the present disclosure.

In operation S410, the CT imaging apparatus 200 generates the second raw data by performing forward projection on the first CT image data from which the to-be-restored region was clipped. Referring to FIGS. 4A-4C, the CT imaging apparatus 200 may form the sinogram 410 by performing forward projection on first CT image data corresponding to the first CT image 400. The second raw data may be the sinogram 410.

In operation S420, the CT imaging apparatus 200 interpolates the pixels corresponding to the to-be-restored region within the second raw data. Referring to FIGS. 4A-4C, the CT imaging apparatus 200 may interpolate the pixel values of the pixels corresponding to the metal trace 411 in the sinogram 410, based on pixel values of pixels adjacent to the pixels corresponding to the metal trace 411. According to an embodiment, the CT imaging apparatus 200 may interpolate the pixel values corresponding to the to-be-restored region by performing linear interpolation. The to-be-restored region may be the metal trace 411.

Figure 5A:
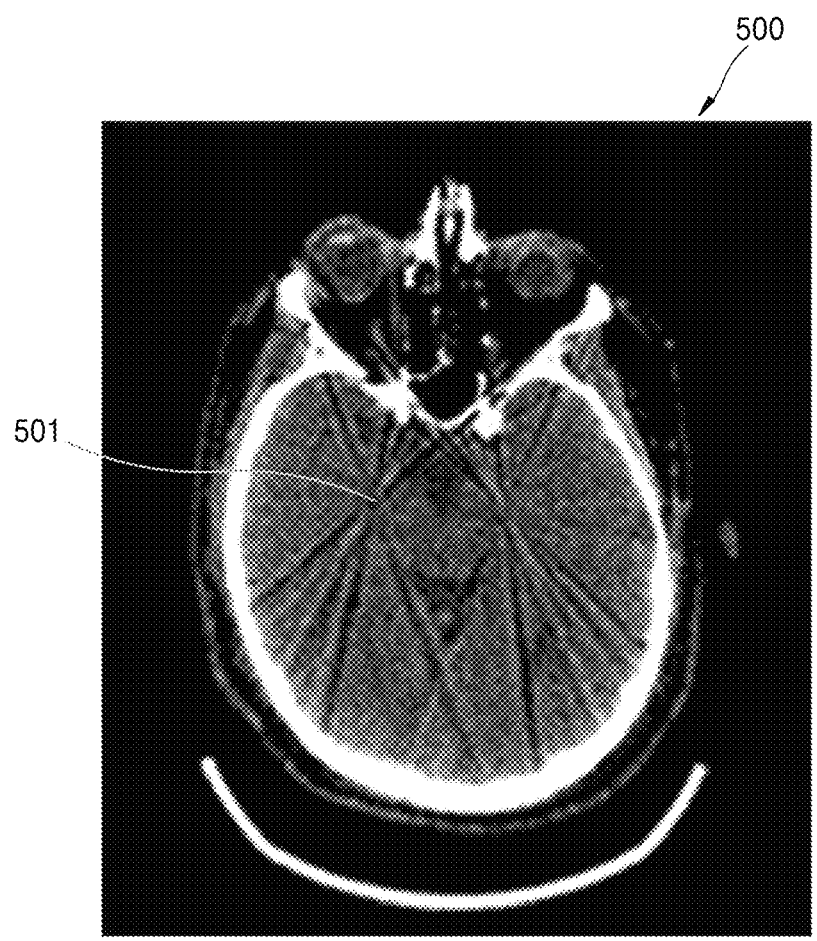
FIGS. 5A-5C are views illustrating a method in which the CT imaging apparatus generates a split image from a CT image, according to an embodiment of the present disclosure.

FIG. 5A illustrates a second CT image 500 that the CT imaging apparatus 200 reconstructs by interpolating the pixel values corresponding to the metal trace 411 of FIG. 4B within the sinogram 410 of FIG. 4B by performing linear interpolation and then performing FBP on the interpolated pixel values.

Referring to FIG. 5A, a to-be-restored region 501 corresponding to the metal trace 411 of FIG. 4B may be displayed relatively darkly on the second CT image 500. The two points representing the metallic implant 401 of FIG. 4A and the to-be-restored region 501 that needs to be restored due to the metal trace 411 of FIG. 4B may degrade the accuracy of the second CT image 500, and make it difficult for the user (for example, a doctor) to ascertain a lesion of a patient from a CT image.

Figure 5B:
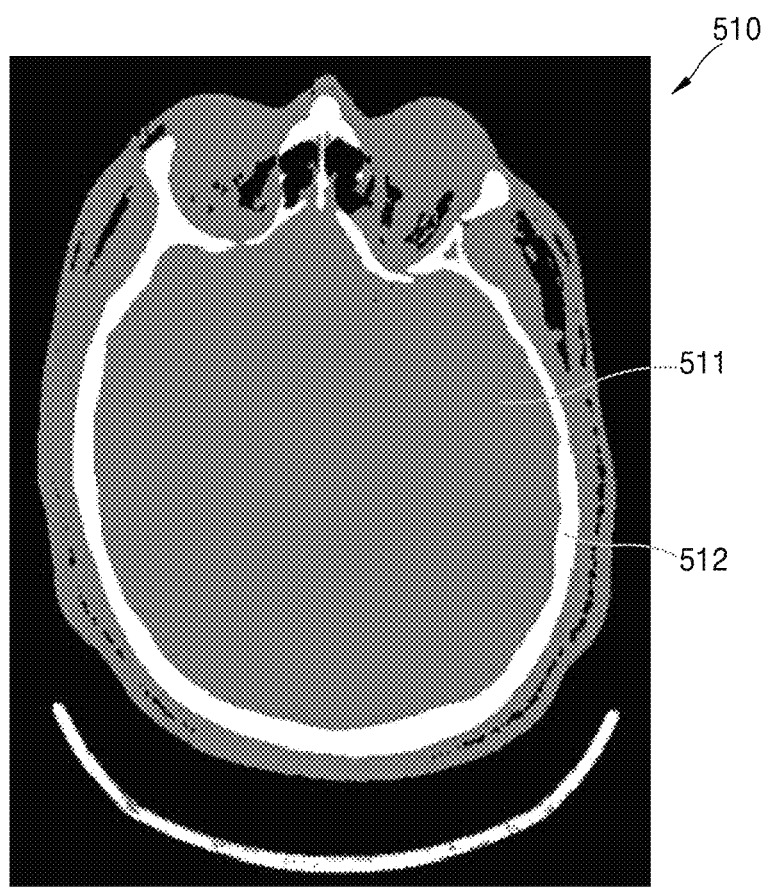

FIG. 5B illustrates a split image 510 generated from the reconstructed second CT image 500 of FIG. 5A, based on an X-ray attenuation degree.

Referring to FIG. 5B, the split image 510 may include a soft tissue 511 and a bone 512 within an object. According to an embodiment, the CT imaging apparatus 200 may set a minimum value or a maximum value of an HU for the second CT image 500 and may split only a corresponding tissue region based on the set minimum or maximum value from the second CT image 500 to thereby generate the split image 510.

As in the embodiment of FIG. 5B, when the CT imaging apparatus 200 sets an HU range to between −100HU and 1000HU, the split image 510 may include the soft tissue 511 and the bone 512.

Figure 5C:
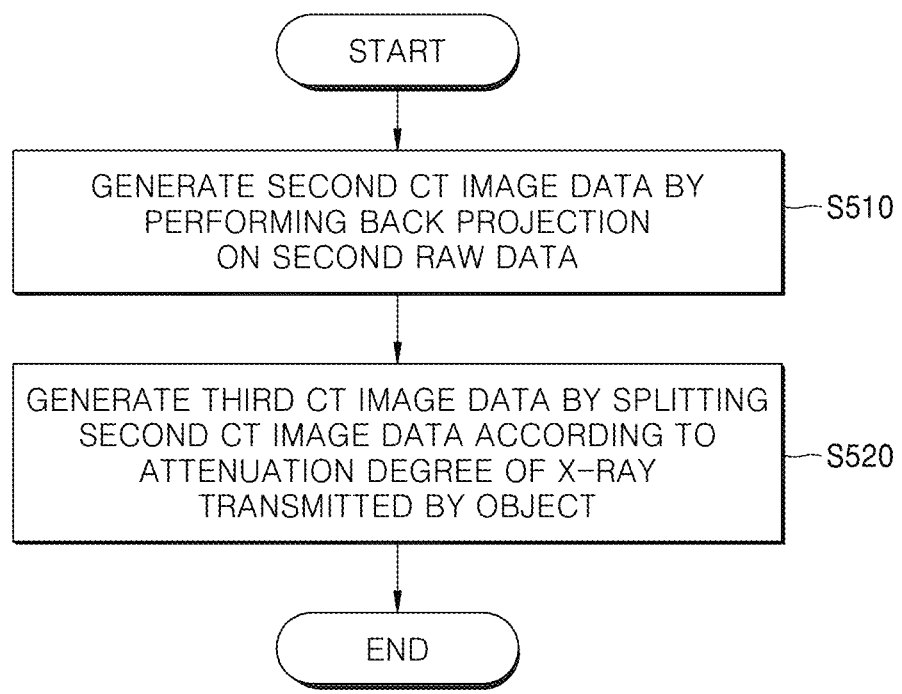

FIG. 5C is a flowchart illustrating a method in which the CT imaging apparatus 200 generates a split image from a CT image, according to an embodiment of the present disclosure.

In operation S510, the CT imaging apparatus 200 generates the second CT image data by performing back projection on the second raw data. Referring to FIGS. 5A and 5C, the CT imaging apparatus 200 may generate the second CT image data by applying FBP to the sinogram 410 of FIG. 4B.

The second raw data may be the sinogram 410, and the second CT image data may be the second CT image 500.

In operation S520, the CT imaging apparatus 200 generates the third CT image data by splitting the second CT image data according to the attenuation degree of the X-ray transmitted by the object. Referring to FIGS. 5B and 5C, the CT imaging apparatus 200 may generate the third CT image data by splitting only a tissue region corresponding to a value that is greater than the minimum value or smaller than the maximum value from the second CT image 500 of FIG. 5A.

Figure 6A:
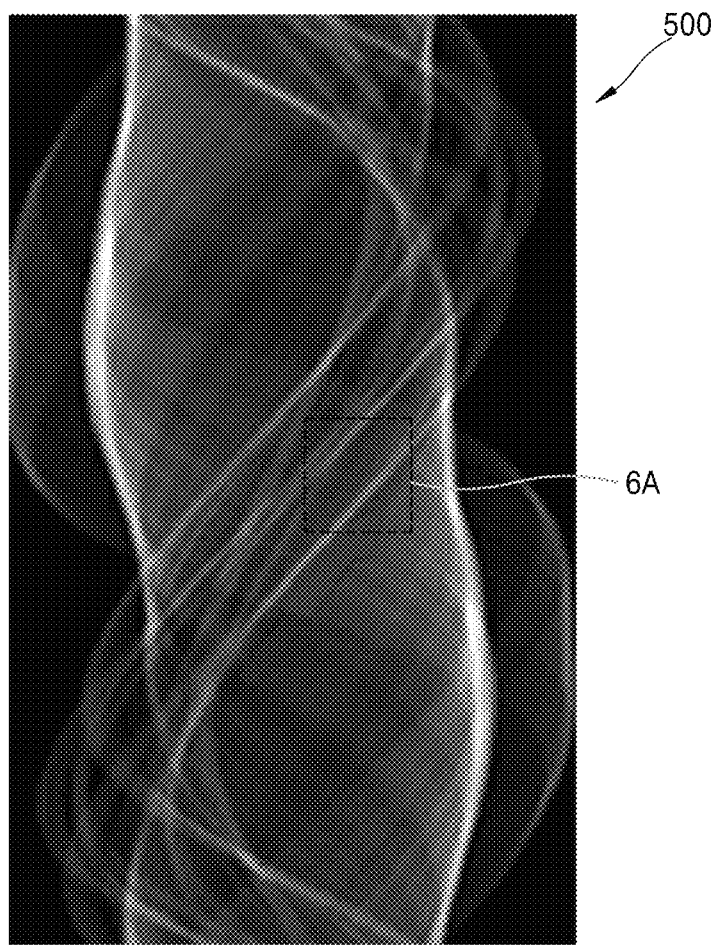
FIGS. 6A and 6B are views illustrating a method in which the CT imaging apparatus obtains direction information from raw data obtained by performing forward projection on a split image, according to an embodiment of the present disclosure.

FIG. 6A illustrates a sinogram 600 that the CT imaging apparatus 200 of FIG. 2 obtains by performing forward projection on the split image 510 of FIG. 5B.

Referring to FIG. 6A, the CT imaging apparatus 200 may generate the reconstructed second CT image 500 of FIG. 5A by interpolating the pixel value of the metal trace 411 of FIG. 4B within the sinogram 410 of FIG. 4B by performing linear interpolation and then performing FBP on the interpolated pixel value, may generate the split image 510 of FIG. 5B by setting an HU from the second CT image 500, and may obtain the sinogram 600 from the split image 510.

The sinogram 600 may include the waveform of the X-ray signal detected by the X-ray detector 113 rotating around the object by 1° at a time by the rotation frame 111 of FIG. 1. The CT imaging apparatus 200 may analyze the waveform of the X-ray signal shown on the sinogram 600 to obtain direction information of the waveform. Directivity of the waveform shown on the sinogram 600 may be obtained based on the pixel values of pixels included in the sinogram 600.

Figure 6B:
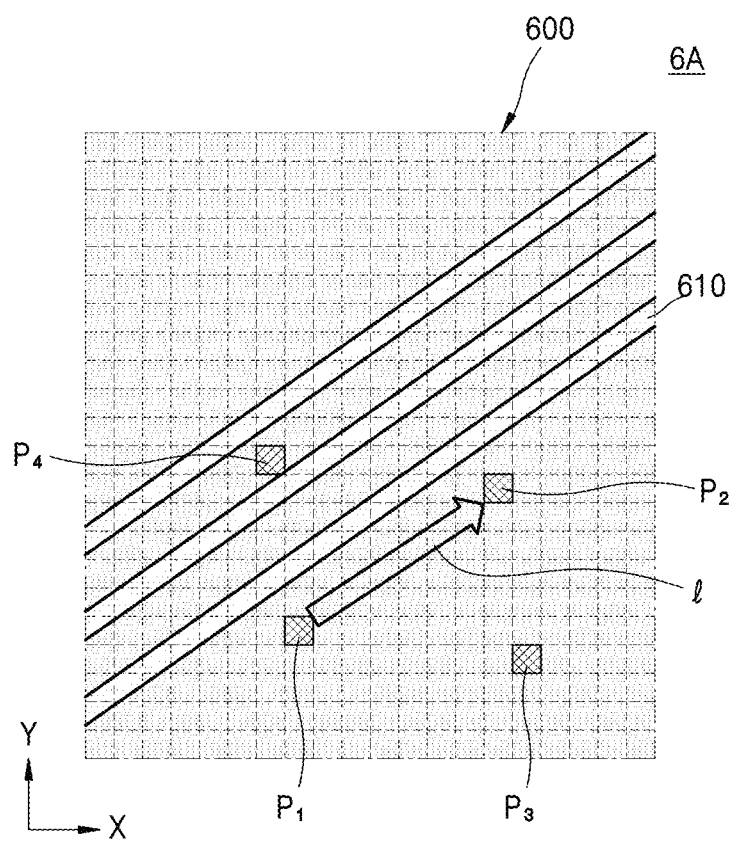

FIG. 6B is a diagram illustrating a method in which the CT imaging apparatus 200 obtains direction information between a plurality of pixels included in a portion 6A of the sinogram 600 of FIG. 6A, according to an embodiment of the present disclosure.

Referring to FIG. 6B, the portion 6A may include a first pixel P1, a second pixel P2, a third pixel P3, a fourth pixel P4, and a plurality of characteristic value waveforms 610. The plurality of characteristic value waveforms 610 may be generated within the sinogram 600 by the X-ray transmission degree due to the difference between the densities of the tissues within the object, and may include a set of a plurality of pixels having relevant pixel values. A pixel value may be a relative value that refers to brightness of each of the pixels generated by the X-ray transmission degree due to the difference between the densities of the tissues within the object. In the case of a pixel having a large pixel value, the large pixel value may be obtained by passing a tissue having a relatively large density within the object along many paths. The pixel value may have a value in the range of, for example, 0 to 5.

According to an embodiment, the CT imaging apparatus 200 may obtain direction information of a virtual line l that connects the first pixel P1 of the sinogram 600 to a pixel whose pixel value varies the least relative to the pixel value of the first pixel P1 from among the second through fourth pixels P2 through P4 adjacent to the first pixel P1 in the first direction (X direction) and the second direction (Y direction). For example, the pixel whose pixel value varies the least relative to the pixel value of the first pixel P1, from among the second through fourth pixels P2 through P4, may be the second pixel P2. The CT imaging apparatus 200 may obtain the direction information of the virtual line l that connects the first pixel P1 to the second pixel P2. According to an embodiment, the direction of the virtual line l may be a direction parallel to the plurality of characteristic value waveforms 610.

According to another embodiment, the CT imaging apparatus 200 may obtain direction information of a virtual line l that connects the first pixel P1 of the sinogram 600 to a pixel having the most similar pixel value to the pixel value of the first pixel P1 from among the second through fourth pixels P2 through P4 adjacent to the first pixel P1 in the first direction (X direction) and the second direction (Y direction). For example, the pixel having the most similar pixel value to the pixel value of the first pixel P1, from among the second through fourth pixels P2 through P4, may be the second pixel P2. The CT imaging apparatus 200 may obtain the direction information of the virtual line l that connects the first pixel P1 to the second pixel P2. According to an embodiment, the direction of the virtual line l may be a direction parallel to the plurality of characteristic value waveforms 610.

Figure 7:
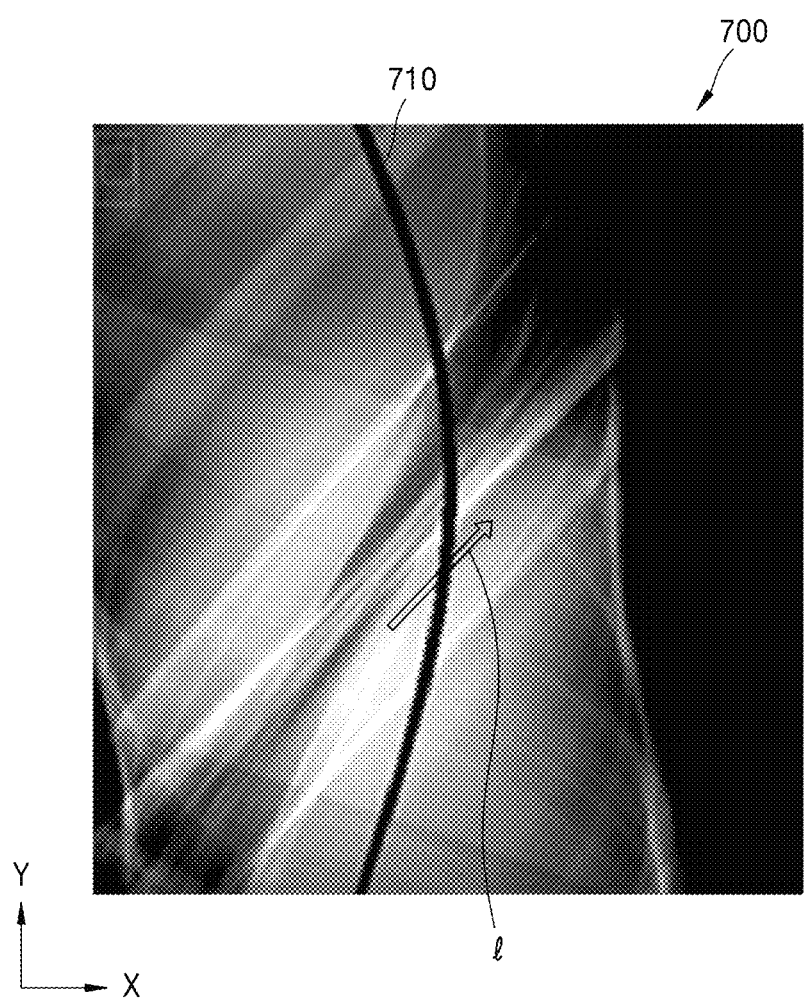
FIG. 7 is an image illustrating a method in which the CT imaging apparatus interpolates pixel values of pixels corresponding to a to-be-restored region in raw data, based on obtained direction information, according to an embodiment of the present disclosure.

FIG. 7 is an image illustrating a method in which the CT imaging apparatus 200 interpolates pixel values of pixels corresponding to a to-be-restored region in raw data, based on obtained direction information, according to an embodiment of the present disclosure.

Referring to FIG. 7, the CT imaging apparatus 200 may interpolate a pixel value of a to-be-restored pixel 710 corresponding to a to-be-restored region in a sinogram 700, based on the direction information of the virtual line 1 obtained in FIG. 6B. The sinogram 700 may be generated by clipping the metallic implant 401 of FIG. 4A set as the to-be-restored region from the first CT image 400 of FIG. 4A and then performing forward projection on the reconstructed first CT image 400.

The pixel value of the to-be-restored pixel 710 within the sinogram 700 may be interpolated by using pixel values of pixels that are adjacent to the to-be-restored pixel 710 in a direction parallel to the direction of the virtual line 1. According to an embodiment, the CT imaging apparatus 200 may interpolate the pixel value of the to-be-restored pixel 710 by performing at least one of linear interpolation, spline interpolation, and polynomial interpolation. However, embodiments are not limited thereto, and the CT imaging apparatus 200 may interpolate pixel values of the to-be-restored pixel 710 by using any of the other well-known interpolation methods.

Figure 8A:
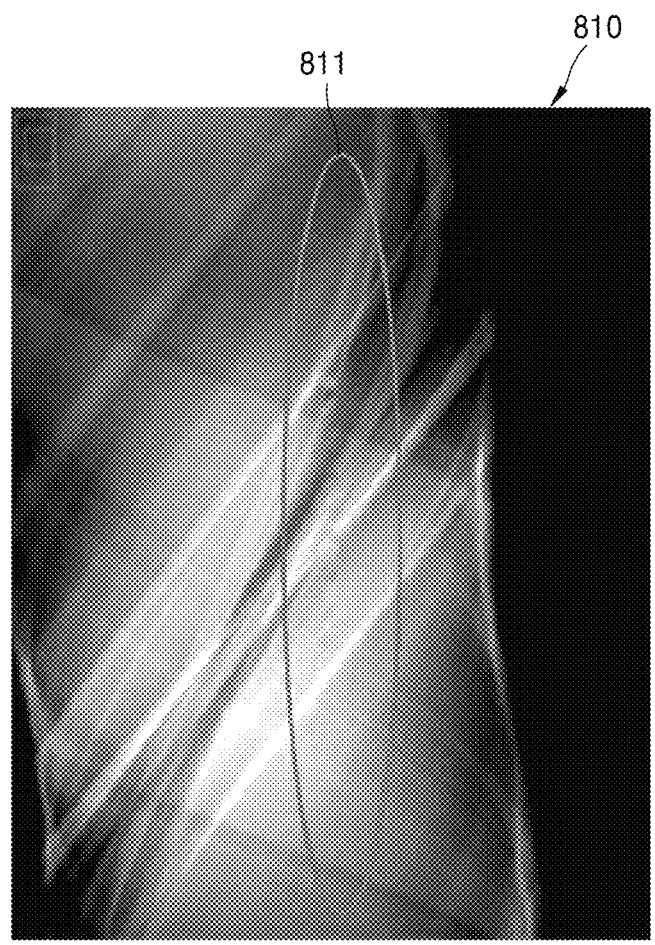
FIG. 8A illustrates a sinogram reconstructed by interpolating a pixel without considering direction information of the sinogram.
Figure 8B:
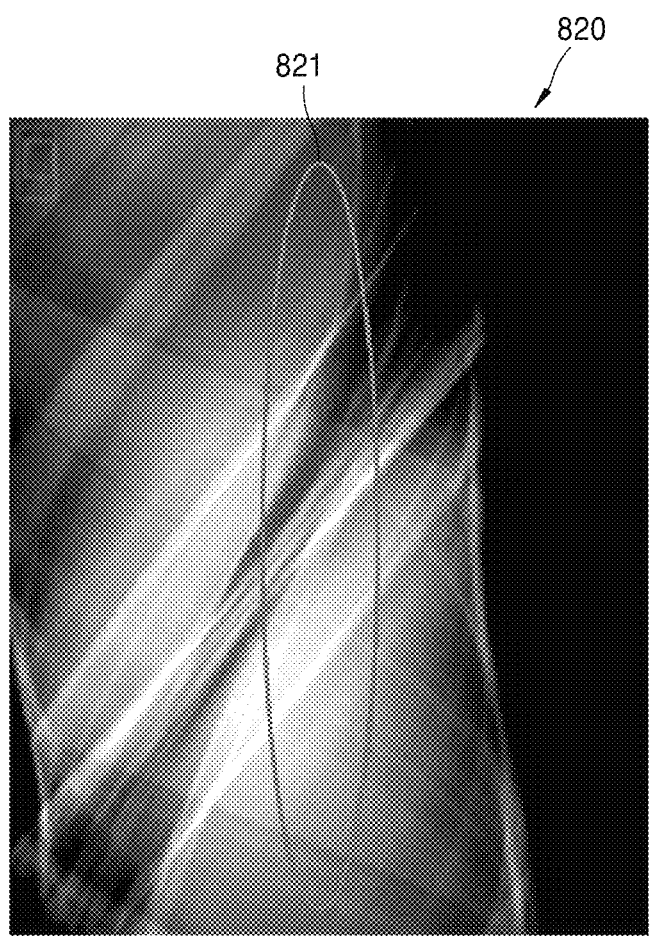
FIG. 8B illustrates a sinogram reconstructed by interpolating a pixel of the sinogram by using a method according to an embodiment of the present disclosure.

FIG. 8A illustrates a sinogram reconstructed by interpolating a pixel without considering direction information of the sinogram, and FIG. 8B illustrates a sinogram reconstructed by interpolating a pixel of the sinogram by using a method according to an embodiment of the present disclosure.

Referring to FIG. 8A, a reconstructed sinogram 810 may include a streak artifact 811 due to metal artifacts. Even when pixel values of pixels corresponding to a metal trace due to metal artifacts have been interpolated, the metal artifacts were incompletely removed from the reconstructed sinogram 810. In this case, an error in estimating a metal trace passing within the sinogram 810 may be large.

FIG. 8B illustrates a reconstructed sinogram 820 that the CT imaging apparatus 200 obtains by interpolating the pixel value of the to-be-restored pixel based on the direction of the virtual line 1 (see FIGS. 6B and 7), according to an embodiment of the present disclosure. Referring to FIG. 8B, a metal trace 821 in the reconstructed sinogram 820 was more naturally interpolated, compared with FIG. 8A.

Because the CT imaging apparatus 200 according to an embodiment of the present disclosure interpolates pixel values of to-be-restored pixels generated due to metal artifacts, based on prior data from the sinogram 600 of FIGS. 6A and 6B before the reconstructed sinogram 820 is formed, namely, based on the direction of the virtual line 1 of FIG. 6B that connects relevant pixels within the sinogram 600 to each other, the CT imaging apparatus 200 may generate a clear final CT image having an improved MAR performance.

FIG. 9 is a flowchart illustrating a method in which the CT imaging apparatus 200 of FIG. 2 generates a final CT image by reconstructing interpolated raw data image, according to an embodiment of the present disclosure.

In operation S910, the CT imaging apparatus 200 interpolates a pixel value of a pixel corresponding to a to-be-restored region, based on direction information. The CT imaging apparatus 200 may interpolate pixel values of to-be-restored pixels interpolated within raw data by performing linear interpolation by using pixel values of neighboring pixels adjacent to the to-be-restored pixels, based on a direction of the virtual line 1 of FIGS. 6B and 7. According to an embodiment, the CT imaging apparatus 200 may interpolate a pixel value of a to-be-restored pixel disposed at a metal trace location, based on a direction of a virtual line 1 that connects the to-be-restored pixel to a pixel whose pixel value varies the least relative to the to-be-restored pixel, from among a plurality of pixels adjacent to to-be-restored pixel. According to another embodiment, the CT imaging apparatus 200 may interpolate the pixel value of the to-be-restored pixel, based on direction information of a virtual line 1 that connects the to-be-restored pixel to a pixel having a similar pixel value to the pixel value of the to-be-restored pixel from among the plurality of pixels adjacent to to-be-restored pixel.

The CT imaging apparatus 200 may interpolate the to-be-restored pixel by performing at least one of linear interpolation, spline interpolation, and polynomial interpolation.

In operation S920, the CT imaging apparatus 200 converts interpolated second raw data into fourth CT image data. According to an embodiment, the second raw data may be a sinogram reconstructed by interpolating pixel values of to-be-restored pixels. The CT imaging apparatus 200 may convert the reconstructed sinogram into the fourth CT image data by performing FBP.

In operation S930, the CT imaging apparatus 200 reconstructs an image by performing a smoothing method including a Gaussian smoothing filter on the fourth CT image data. According to an embodiment, the CT imaging apparatus 200 may reconstruct fourth CT image data by using a median filter and a total variation-based (TV) smoothing method instead of using a Gaussian smoothing filter.

In operation S940, the CT imaging apparatus 200 performs forward projection on a metal trace. According to an embodiment, the CT imaging apparatus 200 may obtain a sinogram by performing forward projection on a metal trace region included in the fourth CT image data. Thereafter, the CT imaging apparatus 200 may perform FBP on the obtained sinogram.

In operation S950, the CT imaging apparatus 200 determines whether the number of iterations i of operations S930 and S940 is greater than a preset number Nitr. When the number of iterations i is smaller than the preset number Nitr (NO), the CT imaging apparatus 200 may repeat operations S930 and S940. In other words, the CT imaging apparatus 200 may perform Gaussian smoothing image-processing on fourth CT image data, perform forward projection on a metal trace within the fourth CT image data, perform FBP on a sinogram, and again perform Gaussian smoothing on fourth CT image data that has undergone the FBP.

When the number of iterations i is greater than the preset number Nitr (YES), the CT imaging apparatus 200 may correct the fourth CT image data by using the to-be-restored region, in operation S960. According to an embodiment, the CT imaging apparatus 200 may insert the to-be-restored region clipped from the first CT image data due to a metallic implant or the like (see operation S310 of FIG. 3) into fourth CT image data that has undergone Gaussian smoothing by the number of iterations i. According to an embodiment, the to-be-restored region may be a metal artifact, such as a metallic implant having a value of about 3000 HU or greater. The CT imaging apparatus 200 may generate a final restored image by inserting the metal artifact into the fourth CT image data.

The above-described embodiments of the present disclosure may be embodied in form of a non-transitory computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

While embodiments of the present disclosure have been particularly shown and described with reference to the accompanying drawings, it will be understood by those of ordinary skill in the art that various changes in form and details may be made therein without departing from the spirit and scope of the present disclosure as defined by the appended claims. The disclosed embodiments should be considered in descriptive sense only and not for purposes of limitation.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A method of operating a computed tomography (CT) imaging apparatus, the method comprising:
generating first CT image data from first raw data received from an X-ray detector and clipping a to-be-restored region from the first CT image data;
generating second raw data and third CT image data based on the first CT image data from which the to-be-restored region was clipped;
obtaining third raw data by performing forward projection on the third CT image data;
obtaining direction information of a virtual line that connects relevant pixels in the third raw data based on pixel values of a plurality of pixels included in the third raw data; and
interpolating a pixel value of a pixel corresponding to the to-be-restored region within the second raw data based on the direction information.

2. The method of claim 1, wherein the clipping of the to-be-restored region comprises setting, in the first CT image data, a region, for which data values representing an attenuation degree of an X-ray transmitted by an object exceed a preset threshold, as the to-be-restored region.

3. The method of claim 1, wherein:
the generating of the second raw data and the third CT image data comprises generating the second raw data by performing forward projection on the first CT image data from which the to-be-restored region was clipped, and the method further comprises interpolating pixels corresponding to the to-be-restored region within the second raw data by performing linear interpolation.

4. The method of claim 1, wherein the generating of the second raw data and the third CT image data comprises:
generating second CT image data by performing backward projection with respect to the second raw data; and
generating the third CT image data split from the second CT image data according to a data value representing an attenuation degree of an X-ray transmitted by an object.

5. The method of claim 4, wherein the generating of the second raw data and the third CT image data comprises separating, from the second CT image data, a tissue region based on a preset minimum or maximum data value.

6. The method of claim 1, wherein the obtaining of the direction information of the virtual line comprises obtaining direction information of the virtual line that connects a first pixel included in the third raw data to a second pixel having a similar pixel value to a pixel value of the first pixel from among pixels that are adjacent to the first pixel in a first direction and a second direction.

7. The method of claim 1, wherein the interpolating of the pixel value comprises interpolating the pixel value of the pixel corresponding to the to-be-restored region by performing at least one of linear interpolation, spline interpolation, or polynomial interpolation.

8. The method of claim 1, further comprising:
generating fourth CT image data by performing back projection on the second raw data; and
reconstructing an image by performing smoothing on the fourth CT image data.

9. The method of claim 8, further comprising modifying the third CT image data using the to-be-restored region clipped from the first CT image data.

10. A computed tomography (CT) imaging apparatus comprising:
a data obtainer configured to obtain first raw data from an X-ray transmitted by an object; and
a processor configured to:
generate first CT image data from the first raw data,
set and clip a to-be-restored region from the first CT image data,
generate second raw data and third CT image data based on the first CT image data from which the to-be-restored region was clipped,
obtain third raw data by performing forward projection on the third CT image data,
obtain direction information of a virtual line that connects relevant pixels in the third raw data based on pixel values of a plurality of pixels included in the third raw data, and
interpolate a pixel value of a pixel corresponding to the to-be-restored region within the second raw data based on the direction information.

11. The CT imaging apparatus of claim 10, wherein the first raw data, the second raw data, and the third raw data are sinograms.

12. The CT imaging apparatus of claim 10, wherein the processor is configured to set, in the first CT image data, a region, for which data values representing an attenuation degree of the X-ray transmitted by the object exceed a preset threshold, as the to-be-restored region.

13. The CT imaging apparatus of claim 10, wherein the processor is configured to:
generate the second raw data by performing forward projection on the first CT image data from which the to-be-restored region was clipped, and
interpolate the pixel value of the pixel corresponding to the to-be-restored region included in the second raw data.

14. The CT imaging apparatus of claim 10, wherein the processor is configured to:
generate second CT image data by performing back projection on the second raw data; and
generate the third CT image data split from the second CT image data according to a data value representing an attenuation degree of the X-ray transmitted by the object.

15. The CT imaging apparatus of claim 14, wherein the processor is configured to separate, from the second CT image data, a tissue region based on a preset minimum or maximum data value.

16. The CT imaging apparatus of claim 10, wherein the processor is configured to obtain direction information of the virtual line that connects a first pixel included in the third raw data to a second pixel having a similar pixel value to a pixel value of the first pixel from among pixels that are adjacent to the first pixel in a first direction and a second direction.

17. The CT imaging apparatus of claim 10, wherein the processor is configured to interpolate the pixel value of the pixel corresponding to the to-be-restored region by performing at least one of linear interpolation, spline interpolation, or polynomial interpolation.

18. The CT imaging apparatus of claim 10, wherein the processor is configured to:
generate fourth CT image data by performing back projection on the second raw data; and
reconstruct an image by performing smoothing on the fourth CT image data.

19. The CT imaging apparatus of claim 18, wherein the processor is configured to modify the third CT image data using the to-be-restored region clipped from the first CT image data.

20. A non-transitory computer-readable recording medium having recorded thereon a program including program code that, when executed, causes a computed tomography (CT) to perform steps including:
generating first CT image data from first raw data received from an X-ray detector and clipping a to-be-restored region from the first CT image data;
generating second raw data and third CT image data based on the first CT image data from which the to-be-restored region was clipped;
obtaining third raw data by performing forward projection on the third CT image data;
obtaining direction information of a virtual line that connects relevant pixels in the third raw data based on pixel values of a plurality of pixels included in the third raw data; and
interpolating a pixel value of a pixel corresponding to the to-be-restored region within the second raw data based on the direction information.

* * * * *